(12) United States Patent
Casonato et al.

(10) Patent No.: US 11,980,373 B2
(45) Date of Patent: May 14, 2024

(54) SURGICAL ASSEMBLY, STABILISATION PLATE AND METHODS

(71) Applicant: 3D METAL PRINTING LIMITED, North East Somerset (GB)

(72) Inventors: Alberto Casonato, Bath (GB); Alisdair R. Macleod, Bath (GB)

(73) Assignee: 3D Metal Printing Limited, Bath (GB)

( * ) Notice: Subject to any disclaimer, the term of this patent is extended or adjusted under 35 U.S.C. 154(b) by 0 days.

(21) Appl. No.: 17/684,162

(22) Filed: Mar. 1, 2022

(65) Prior Publication Data

US 2022/0280167 A1 Sep. 8, 2022

Related U.S. Application Data

(63) Continuation of application No. 16/312,160, filed as application No. PCT/GB2017/051806 on Jun. 20, 2017, now Pat. No. 11,602,354.

(30) Foreign Application Priority Data

Jun. 21, 2016 (GB) ...................................... 1610809

(51) Int. Cl.
*A61B 17/15* (2006.01)
*A61B 17/80* (2006.01)
*A61B 17/56* (2006.01)
*A61B 90/00* (2016.01)

(52) U.S. Cl.
CPC ........ *A61B 17/151* (2013.01); *A61B 17/8095* (2013.01); *A61B 2017/568* (2013.01); *A61B 17/8061* (2013.01); *A61B 2090/037* (2016.02)

(58) Field of Classification Search
CPC .... A61B 17/151; A61B 7/152; A61B 17/8095
See application file for complete search history.

(56) References Cited

U.S. PATENT DOCUMENTS 4,653,488 A * 3/1987 Kenna .................. A61B 17/154
606/88

* cited by examiner

*Primary Examiner* — Matthew J Lawson
(74) *Attorney, Agent, or Firm* — Gable Gotwals; David G. Woodral

(57) ABSTRACT

A surgical assembly, a stabilisation plate and methods. The surgical assembly comprises includes a jig having a body with a tissue-engaging surface shaped to be received by tissue to be re-orientated by a correction factor. The body defines a plurality of alignment apertures orientated to be parallel with respect to each other on application of said correction factor.

19 Claims, 8 Drawing Sheets

SURGICAL ASSEMBLY, STABILISATION PLATE AND METHODS

CROSS-REFERENCE TO RELATED CASES

This application is a continuation of U.S. patent application Ser. No. 16/312,160 entitled SURGICAL ASSEMBLY, STABILISATION PLATE AND METHODS filed on Dec. 20, 2018 which claims the benefit of a 35 U.S.C. § 371 National Stage Entry of PCT/GB2017/051806 entitled A SURGICAL ASSEMBLY, STABILISATION PLATE AND METHODS filed on Jun. 20, 2017, which claims priority to GB Patent Application No. 1610809.4 entitled A SURGICAL ASSEMBLY, STABILISATION PLATE AND METHODS filed on Jun. 21, 2016, the contents of which are hereby incorporated by reference.

FIELD OF THE INVENTION

The present invention relates to a surgical assembly, a stabilisation plate and methods.

BACKGROUND OF THE INVENTION

Surgical assemblies are known. Such assemblies are typically utilised in various surgical procedures. Although surgical assemblies are known to assist with surgical procedures, they each have their own shortcomings. Accordingly, it is desired to provide an improved surgical assembly.

SUMMARY OF THE INVENTION

According to a first aspect, there is provided a surgical assembly, comprising: a jig comprising a body having a tissue-engaging surface shaped to be received by tissue to be re-orientated by a correction factor, the body defining a plurality of alignment apertures, the plurality of alignment apertures being orientated to be parallel with respect to each other on application of the correction factor.

The first aspect recognises that one such surgical procedure occurs to correct a mis-orientation of tissue. For example, soft tissue or bone may need to be re-orientated for various reasons in order to improve the well-being of a patient. Such re-orientation can be problematic since, even with the most skilled surgeons, it can be difficult to determine whether the appropriate correction has been applied in order to re-orientate the tissue without performing operative measurements and/or imaging, which is often difficult and time-consuming to do.

Accordingly, a surgical assembly or kit is provided. The assembly may comprise a jig or guide structure. The jig may have a body or structure which has a surface which is shaped to be received or co-operate with the tissue to be re-orientated by the application of a correction factor, rotation or a displacement of the tissue. The body may also define or be provided with at least two alignment apertures or conduits. The alignment apertures may be orientated or angled with respect to each other so that they become parallel with each other once the correction factor has been applied. In this way, it is possible to determine from the jig itself when the desired correction factor, rotation or displacement has been applied correctly because the alignment apertures become parallel, thereby avoiding the need for additional operative measurement and/or imaging.

In one embodiment, the plurality of alignment apertures are orientated to be parallel with respect to each other on application of the correction factor to the tissue.

In one embodiment, each alignment aperture is arranged to receive an alignment shaft to engage with the tissue. Accordingly, each alignment aperture or conduit may receive a shaft which may engage with or be retained by the tissue. Hence, the alignment apertures determine the position and orientation of the alignment shafts with respect to the tissue.

In one embodiment, the plurality of alignment apertures are orientated to orientate each alignment shaft to be parallel with respect to each other on application of the correction factor. Accordingly, the jig may be retained by the alignment shafts on the tissue prior to the application of the correction factor, but may then freely slide along the alignment shafts when the desired correction factor has been applied to the tissue since they then become parallel. Hence, the ability of the jig to disengage from the alignment shafts provides an indication that the required correction factor has been applied correctly, again without the need for any operative measurements and/or imaging.

In one embodiment, the plurality of alignment apertures are orientated to orientate each alignment shaft to be parallel with respect to each other on application of the correction factor to the tissue.

In one embodiment, the plurality of alignment apertures are orientated to be divergent in an uncorrected position prior to application of the correction factor and to be parallel in a corrected position on application of the correction factor. Arranging for the alignment apertures to be non-parallel or divergent in the uncorrected position helps to resist the removal of the jig from the alignment shafts when the tissue is anything other than correctly realigned.

In one embodiment, the alignment apertures extend between the tissue-engaging surface and an interaction surface opposing the tissue-engaging surface. Hence the apertures extend through the body, from one surface to another.

In one embodiment, each alignment aperture has a length selected to control a depth of the alignment shafts into the tissue. Accordingly, the length of the aperture may be selected in order to vary the depth that each alignment shaft enters the tissue.

In one embodiment, the body comprises a first body portion shaped to be received by a first tissue portion of the tissue and a second body portion shaped to be received by a second tissue portion of the tissue, the first body portion being re-orientatable with respect to the second body portion to re-orientate the first tissue portion with respect to the second tissue portion by the correction factor. Accordingly, the body may be formed of two independently-orientatable body portions, each of which engages with a respective portion of the tissue. The body may be flexible to facilitate re-orientation of the first and second body portions. Re-orientation of one of the body portions with respect to the other causes a respective re-orientation of the tissue portions in order to achieve the correction or realignment required.

In one embodiment, the first body portion and the second body portion each comprise at least one of the plurality of alignment apertures. Accordingly, each of the body portions may be provided with one or more of the alignment apertures in order to facilitate determining the correct realignment of the body portions.

In one embodiment, the correction factor comprises an angular displacement about at least one axis. Accordingly, the correction factor may be a rotation about at least one axis of the tissue.

In one embodiment, the jig defines a cutting aperture shaped to receive a cutting device operable to at least partially divide the tissue into the first tissue portion and the second tissue portion. Accordingly, when the tissue is insufficiently flexible to be re-orientated, the jig may be provided with a cutting aperture or guide which is shaped to receive a cutting device which may cut or divide the tissue into the first and second tissue portions in order to facilitate the re-orientation of the tissue.

In one embodiment, the cutting aperture is positioned between the first body portion and the second body portion. In other words, the first and second body portions sit adjacent the cutting aperture so that they are proximate any tissue cut.

In one embodiment, the cutting aperture is dimensioned to provide a close fit with the cutting device. Providing a close fit helps to accurately control the location of the cutting device.

In one embodiment, the cutting aperture is orientated to orientate the cutting device with respect to the tissue. Accordingly, the aperture may angle the cutting device with respect to the tissue. In embodiments, the angle of cut may vary along the cutting aperture.

In one embodiment, the cutting aperture extends between the tissue-engaging surface and an interaction surface opposing the tissue-engaging surface. Hence the aperture extend through the body, from one surface to another.

In one embodiment, a depth of the cutting aperture is dimensioned to retain a hinge portion joining the first tissue portion with the second tissue portion. Accordingly, the depth of the cutting aperture may be set in order to prevent the tissue from being completely separated and instead to retain a hinge portion or region which joins the tissue portions together.

In one embodiment, the depth of the cutting aperture is varied to retain the hinge portion joining the first tissue portion with the second tissue portion. Accordingly, the depth of the cutting aperture may be changed along its length in order to ensure that the hinge portion is retained and to prevent damage to any adjacent tissue.

In one embodiment, the body comprises a re-orientation mechanism operable to re-orientate the first body portion with respect to the second body portion to re-orientate the first tissue portion with respect to the second tissue portion by the correction factor. Accordingly, the jig itself may have an inbuilt mechanism which is used to re-orientate the first and second body portions in order to re-orientate the two tissue portions by the required correction factor. This helps to simplify the procedure by requiring fewer additional instruments.

In one embodiment, the re-orientation mechanism is operable to displace the first body portion with respect to the second body portion. Accordingly, the re-orientation mechanism may simply displace the two body portions by the required correction factor.

In one embodiment, the re-orientation mechanism comprises at least one re-orientation aperture defined by one of the first body portion and the second body portion and operable to receive a re-orientation shaft extendible from the re-orientation aperture by a distance to engage with another of the first body portion and the second body portion to re-orientate the first body portion with respect to the second body portion. Accordingly, at least one shaft extending from one body portion to engage with the other may simply be actuated in order to re-orientate the two body portions with respect to each other and perform the required correction.

In one embodiment, the re-orientation mechanism comprises at least one re-orientation shaft receiver defined by the another of the first body portion and the second body portion and shaped to engage with the re-orientation shaft. Providing a re-orientation shaft receiver helps to ensure engagement between the two portions and improve the accuracy of performing the required correction.

In one embodiment, the body comprises a plurality of the re-orientation apertures and the re-orientation shaft receivers. Hence, the mechanism may be actuated at many different locations to perform the required correction precisely.

In one embodiment, the body comprises at least one wedge aperture dimensioned to receive a wedge. Accordingly, apertures may be provided within the body which are dimensioned, configured or shaped to receive a wedge. The apertures extend through the body, from one surface to another.

In one embodiment, each wedge aperture is positioned between the first body portion and the second body portion. Accordingly, each wedge aperture may be located between the body portions. The wedge aperture may be located adjacent the cutting aperture.

In one embodiment, the assembly comprises at least one wedge dimensioned to be received by a corresponding wedge aperture. Accordingly, a wedge may be provided which is dimensioned or configured to be received or engage with a corresponding or associated wedge aperture.

In one embodiment, the wedge comprises a receiving portion dimensioned to be received by the corresponding wedge aperture and a protruding portion dimensioned to extend into the tissue to retain the correction factor. Accordingly, the wedge may have a part which fits the wedge aperture, together with a protruding or extending part which extends in to the cut made into the tissue in order to hold the portions of the tissue re-orientated with the required correction factor.

In one embodiment, the wedge comprises an abutment portion coupling the receiving portion and the protruding portion and operable to engage with a facing surface of the tissue. Accordingly, the wedge may be provided with an abutment or contacting part which contacts the tissue and controls the depth to which the protruding portion enters the cut.

In one embodiment, the assembly comprises a plurality of the wedge apertures and a corresponding plurality of the wedges.

In one embodiment, each of the plurality of the wedge apertures is configured to receive only a corresponding wedge. Accordingly, each wedge aperture and corresponding wedge may be uniquely matched such that each wedge will only fit in to one associated or corresponding aperture. This helps to prevent a wedge being located in an incorrect aperture.

In one embodiment, the body comprises a retention portion operable to retain the first body portion with the second body portion until separated. Accordingly, the two body portions may be coupled using a fixing portion, which holds the two portions together until they are required to be separated to facilitate the application of the correction factor and/or the removal of the jig.

In one embodiment, the body comprises at least one fixing aperture arranged to receive a shaft to engage with the tissue. Accordingly, fixing apertures may also be provided on the body. The fixing apertures may receive shafts which engage with the tissue in order to provide additional fixing of either the jig or the stabilising plate to the tissue.

In one embodiment, each fixing aperture extends between the tissue-engaging surface and an interaction surface opposing the tissue-engaging surface. Hence the apertures extend through the body, from one surface to another.

In one embodiment, each fixing aperture has a length selected to control a depth of the shafts into the tissue.

In one embodiment, an orientation of a plurality of the fixing apertures diverges. Providing divergent fixing apertures helps to improve the fixing of the jig and/or the stabilising plate on to the tissue.

In one embodiment, the tissue-engaging surface is shaped for close-engagement with contours of the tissue. Accordingly, the tissue-engaging surface of the jig may be shaped to match the contours of the tissue using, for example, 3-D printing techniques and the contour information provided from imaging scans.

In one embodiment, the assembly comprises a stabilisation plate having plate alignment apertures positioned to receive each alignment shaft on application of the correction factor to the tissue. Accordingly, a stabilisation plate may also be provided which has alignment apertures which are positioned to align with the alignment shafts when the required correction factor has been applied to the tissue. In this way, the stabilisation plate can only be fitted if the tissue has been correctly realigned. This again helps to ensure that the stabilisation plate can only be fitted when the required correction factor has been applied and also avoids the need for any operative measurements and/or imaging.

In one embodiment, the stabilisation plate comprises plate fixing apertures positioned to align with voids created by the shafts on application of the correction factor to the tissue. Accordingly, once again, the fixing apertures of the stabilisation plate will only align with the voids if the required correction factor has been applied to the tissue. This again helps to ensure that the stabilisation plate can only be fitted when the required correction factor has been applied and also avoids the need for any operative measurements and/or imaging.

In one embodiment, the stabilisation plate comprises a tissue-engaging surface shaped for close-engagement with contours of the tissue. Accordingly, the surface of the stabilisation plate may also be shaped to engage with the tissue using, for example, 3-D printing techniques and the contour information provided from imaging scans.

In one embodiment, the assembly comprises an elongate position locator having a tissue-engagement structure operable to engage with a location of the tissue and a jig engagement structure operable to engage with the jig, the elongate position locator being dimensioned to locate the jig at a position on the tissue. Accordingly, the elongate position locator helps to precisely locate the jig at the correct location on the tissue.

According to a second aspect, there is provided a surgical stabilisation plate, comprising: plate alignment apertures positioned to receive a plurality of alignment shafts extending from a tissue on application of a correction factor to the tissue.

In one embodiment, the surgical stabilisation plate comprises plate fixing apertures positioned to align with voids in the tissue on application of the correction factor to the tissue.

In one embodiment, the stabilisation plate comprises a tissue-engaging surface shaped for close-engagement with contours of the tissue.

Embodiments of the second aspect provide features corresponding to features of the first aspect.

According to a third aspect, there is provided a method comprising: forming a jig comprising a body; shaping a tissue-engaging surface of the body to be received by tissue to be re-orientated by a correction factor; defining a plurality of alignment apertures in the body and orientating the plurality of alignment apertures to be parallel with respect to each other on application of the correction factor.

In one embodiment, the method comprises determining the correction factor by measuring a misorientation of the tissue.

In one embodiment, the method comprises determining the correction factor by measuring a deviation of a centre of a tissue mid-joint from an axis extending between two tissue end-joints.

In one embodiment, the orientating comprises orientating the plurality of alignment apertures to be parallel with respect to each other on application of the correction factor to the tissue.

In one embodiment, the method comprises arranging each alignment aperture to receive an alignment shaft to engage with the tissue.

In one embodiment, the method comprises orientating the plurality of alignment apertures to orientate each alignment shaft to be parallel with respect to each other on application of the correction factor.

In one embodiment, the method comprises orientating the plurality of alignment apertures to orientate each alignment shaft to be parallel with respect to each other on application of the correction factor to the tissue.

In one embodiment, the method comprises orientating the plurality of alignment apertures to be divergent in an uncorrected position prior to application of the correction factor and to be parallel in a corrected position on application of the correction factor.

In one embodiment, the method comprises extending the alignment apertures between the tissue-engaging surface and an interaction surface opposing the tissue-engaging surface.

In one embodiment, the method comprises selecting a length of each alignment aperture to control a depth of the alignment shafts into the tissue.

In one embodiment, the forming comprises forming a first body portion shaped to be received by a first tissue portion of the tissue and a second body portion shaped to be received by a second tissue portion of the tissue, the first body portion being re-orientatable with respect to the second body portion to re-orientate the first tissue portion with respect to the second tissue portion by the correction factor.

In one embodiment, the first body portion and the second body portion each comprise at least one of the plurality of alignment apertures.

In one embodiment, the correction factor comprises an angular displacement or rotation about at least one axis.

In one embodiment, the method comprises defining a cutting aperture shaped to receive a cutting device operable to at least partially divide the tissue into the first tissue portion and the second tissue portion.

In one embodiment, the method comprises positioning the cutting aperture between the first body portion and the second body portion.

In one embodiment, the method comprises dimensioning the cutting aperture to provide a close fit with the cutting device.

In one embodiment, the method comprises orientating the cutting aperture to orientate the cutting device with respect to the tissue.

In one embodiment, the method comprises extending the cutting aperture between the tissue-engaging surface and an interaction surface opposing the tissue-engaging surface.

In one embodiment, the method comprises dimensioning a depth of the cutting aperture to retain a hinge portion joining the first tissue portion with the second tissue portion.

In one embodiment, the method comprises varying the depth of the cutting aperture to retain the hinge portion joining the first tissue portion with the second tissue portion.

In one embodiment, the method comprises providing a re-orientation mechanism operable to re-orientate the first body portion with respect to the second body portion to re-orientate the first tissue portion with respect to the second tissue portion by the correction factor.

In one embodiment, the re-orientation mechanism is operable to displace the first body portion with respect to the second body portion.

In one embodiment, the providing the re-orientation mechanism comprises defining at least one re-orientation aperture within one of the first body portion and the second body portion, the at least one re-orientation aperture being operable to receive a re-orientation shaft extendible from the re-orientation aperture by a distance to engage with another of the first body portion and the second body portion to re-orientate the first body portion with respect to the second body portion.

In one embodiment, the providing the re-orientation mechanism comprises defining at least one re-orientation shaft receiver within the another of the first body portion and the second body portion and shaping the at least one re-orientation shaft receiver to engage with the re-orientation shaft.

In one embodiment, the providing the re-orientation mechanism comprises defining a plurality of the re-orientation apertures and the re-orientation shaft receivers.

In one embodiment, the method comprises dimensioning at least one wedge aperture to receive a wedge.

In one embodiment, the method comprises positioning the wedge aperture between the first body portion and the second body portion.

In one embodiment, the method comprises providing at least one wedge dimensioned to be received by a corresponding wedge aperture.

In one embodiment, the method comprises dimensioning the wedge with a receiving portion to be received by the corresponding wedge aperture and a protruding portion to extend into the tissue to retain the correction factor.

In one embodiment, the method comprises forming the wedge with an abutment portion coupling the receiving portion and the protruding portion and configured to engage with a facing surface of the tissue.

In one embodiment, the method comprises forming a plurality of the wedge apertures and providing a corresponding plurality of the wedges.

In one embodiment, the method comprises configuring each of the plurality of the wedge apertures to receive only a corresponding wedge.

In one embodiment, the method comprises forming a retention portion to retain the first body portion with the second body portion until separated.

In one embodiment, the method comprises forming at least one fixing aperture to receive a shaft to engage with the tissue.

In one embodiment, the method comprises extending each fixing aperture between the tissue-engaging surface and an interaction surface opposing the tissue-engaging surface.

In one embodiment, the forming comprises forming each fixing aperture with a length selected to control a depth of the shafts into the tissue.

In one embodiment, the method comprises diverging an orientation of a plurality of the fixing apertures.

In one embodiment, the method comprises shaping the tissue-engaging surface for close-engagement with contours of the tissue.

In one embodiment, the method comprises providing a stabilisation plate having plate alignment apertures positioned to receive each alignment shaft on application of the correction factor to the tissue.

In one embodiment, the method comprises positioning plate fixing apertures to align with voids created by the shafts on application of the correction factor to the tissue.

In one embodiment, the method comprises shaping the stabilisation plate with a tissue-engaging surface for close-engagement with contours of the tissue.

In one embodiment, the method comprises providing an elongate position locator having a tissue-engagement structure arranged to engage with a location of the tissue and a jig engagement structure operable to engage with the jig, the elongate position locator being dimensioned to locate the jig at a position on the tissue.

In one embodiment, the method comprises optimising the configuration of the stabilisation plate based on patient characteristics.

In one embodiment, the patient characteristics comprise at least one of weight, activity level and bone quality.

According to a fourth aspect, there is provided a method, comprising: locating a jig on a tissue to be re-orientated by a correction factor, the jig comprising a body having a tissue-engaging surface shaped to be received on the tissue, the body defining a plurality of alignment apertures, the plurality of alignment apertures being orientated to be parallel with respect to each other on application of the correction factor.

In one embodiment, the locating comprises locating using an elongate position locator having a tissue-engagement structure arranged to engage with a location of the tissue and a jig engagement structure operable to engage with the jig, the elongate position locator being dimensioned to locate the jig at a position on the tissue.

In one embodiment, the body comprises at least one fixing aperture, the method comprising receiving a fixing shaft within each fixing aperture to engage with the tissue and retain the jig on the tissue.

In one embodiment, the method comprises receiving an alignment shaft within each alignment aperture to engage with the tissue.

In one embodiment, the body comprises a first body portion shaped to be received by a first tissue portion of the tissue and a second body portion shaped to be received by a second tissue portion of the tissue, the first body portion being re-orientatable with respect to the second body portion to re-orientate the first tissue portion with respect to the second tissue portion by the correction factor.

In one embodiment, the method comprises manipulating the jig to perform the correction factor.

In one embodiment, the correction factor comprises an angular displacement rotation about at least one axis.

In one embodiment, the jig defines a cutting aperture shaped to receive a cutting device operable to at least partially divide the tissue into the first tissue portion and the second tissue portion and the method comprises, prior to the manipulation, inserting the cutting device into the cutting aperture to at least partially divide the tissue.

In one embodiment, the body comprises a re-orientation mechanism operable to re-orientate the first body portion with respect to the second body portion to re-orientate the first tissue portion with respect to the second tissue portion by the correction factor and the manipulation comprises operating the re-orientation mechanism.

In one embodiment, the body comprises at least one wedge aperture dimensioned to receive a wedge and the method comprises inserting a wedge into each wedge aperture.

In one embodiment, the method comprises removing the fixing shafts and removing the jig from the tissue, along the alignment shafts.

In one embodiment, the method comprises fitting a stabilisation plate having plate alignment apertures positioned to receive each alignment shaft on application of the correction factor to the tissue.

In one embodiment, the method comprises fitting fixings into fixing apertures of the stabilisation plate.

In one embodiment, the method comprises replacing each alignment shaft with a fixing.

In one embodiment, the method comprises removing each wedge.

In one embodiment, the method is an in vivo method.

In one embodiment, the method is not practised on the human or animal body.

In one embodiment, the method is an in vitro method.

In one embodiment, the method is an ex-vivo method.

Embodiments of the fourth aspect provide features corresponding to features of the first and/or second aspect and/or third aspect.

Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

BRIEF DESCRIPTION OF THE DRAWINGS

Embodiments of the present invention will now be described further, with reference to the accompanying drawings, in which.

DETAILED DESCRIPTION OF THE PREFERRED EMBODIMENTS

Overview

Figure 1:
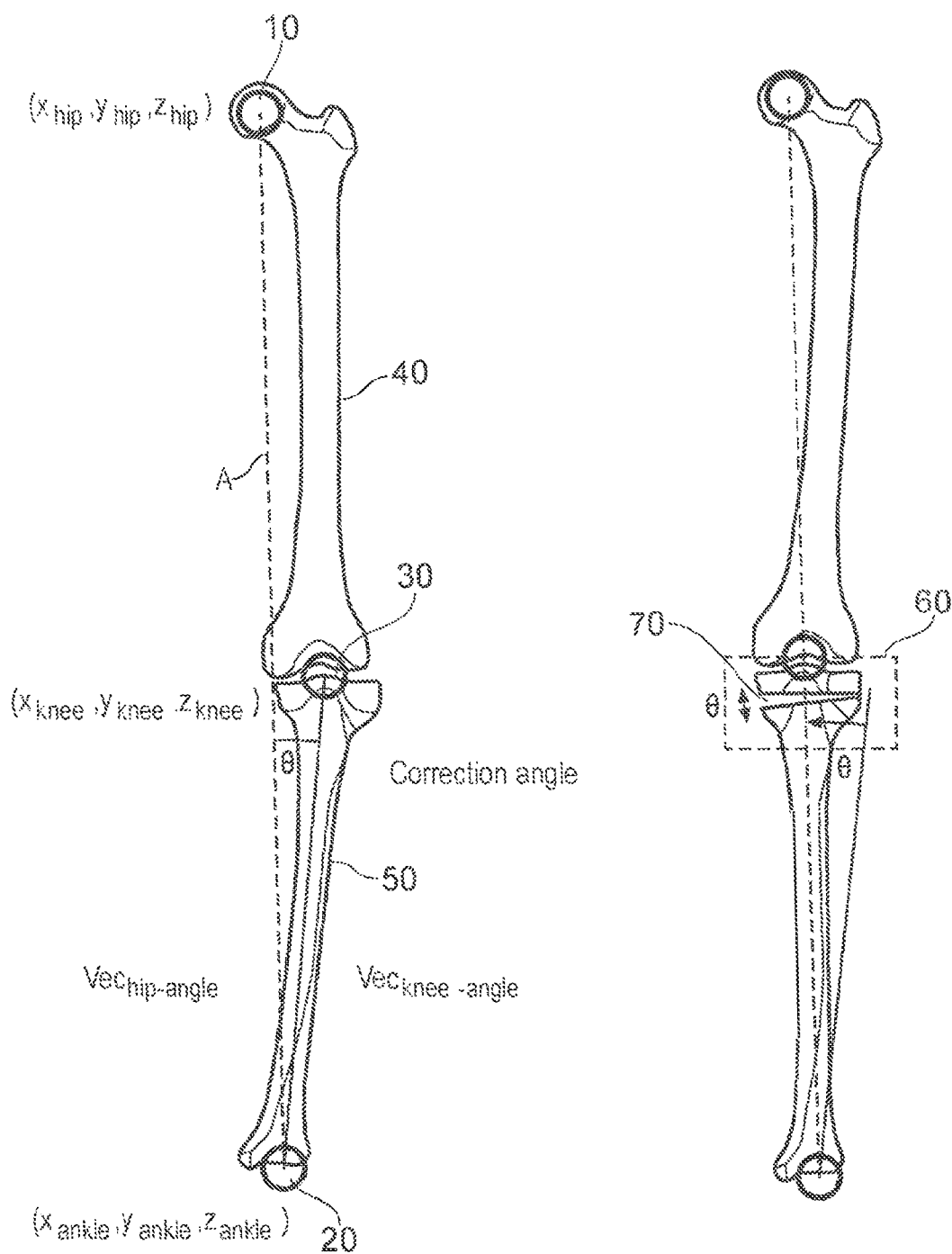
FIG. 1 shows a representation of a scan and illustrates a tissue correction.

Before discussing embodiments in any more detail, first an overview will be provided. Embodiments provide a technique for changing, adjusting or rotating the alignment or direction of a tissue. That change may be to align tissue or to correct misaligned tissue. The technique utilises an assembly whose main components are a jig and associated components, together with a stabilisation plate.

Typically, the tissue to be realigned is first imaged or examined in order that the correction to be applied to the tissue is determined. Typically, the data from the imaging is used to create a 3D model of the tissue in it uncorrected form. The point or region about which the correction is to occur is selected on the tissue. That correction will typically be that one portion of the tissue on one side of the point or region is to be pivoted or translated with respect to another portion of the tissue on another side of the point or region in order to align the tissue or correct a misalignment. Such pivoting will typically occur in three dimensions and can be normally be expressed as a rotation of one portion of the tissue with respect to the other portion of the tissue by a specified angle in each of three dimensions using conventional geometric analysis. It will be appreciated that in some circumstances, the rotation required may be in fewer than three dimensions. The 3D model of the tissue can then be manipulated to show the tissue in its corrected form.

A jig is designed to fit with the tissue adjacent the region or point about which the rotation is to occur. The jig is typically designed using 3D modelling techniques which incorporate the 3D model of the tissue in its corrected and uncorrected form. In particular, the jig is formed of two parts, which are positioned on either side of the region or point about which the rotation is to occur. Once the general size and external shape of the jig has been defined in the 3D model, alignment apertures are provided within the jig, through which alignment shafts extend into the tissue. The geometry of those apertures is determined using conventional geometric analysis so that the shafts are only parallel once the required correction has been made to the tissue; otherwise, the shafts are divergent. This means that when the required correction has not been correctly made, the orientation of the shafts in the alignment apertures resists the removal of the jig from the tissue. However, once the required correction has been made the jig can be removed from the alignment shafts. This arrangement ensures that the required correction can easily be made and verified without the need for any further imaging and/or measurements. The jig is then created, typically using 3D printing techniques.

A stabilisation plate is designed to fit with the tissue adjacent the region or point about which the rotation is to occur. The stabilisation plate is typically designed using 3D modelling techniques which incorporate the 3D model of the tissue in its corrected form. The stabilisation plate also has alignment apertures which match the position of the alignment shafts when in the corrected position. Once the jig has been removed, then the stabilisation plate can be received by the alignment shafts only if the required correction has still been made. This again ensures that the stabilisation plate can only be fitted when the required correction has been made and provides assurance that the correction remains true during the fitting of the stabilisation plate, without the need for any further measurements and/or imaging. The alignment shafts may then be used to help fix the stabilisation plate or removed and permanent fixings for the stabilisation plate inserted in their place. The stabilisation plate is then created, typically using 3D printing techniques.

Embodiments provide a re-orientation mechanism to re-orientate one part of the jig with respect to the other part of the jig by the required amount in order to perform the required correction to the tissue. Typically, a self-contained mechanical displacement arrangement is provided which, when activated, rotates and/or displaces one part of the jig with respect to the other part of the jig about the point or region the tissue in order to perform the required correction. The arrangement of the re-orientation mechanism can also readily be determined using conventional geometric analysis. The assembly may also comprise a supporting structure which supports the tissue in the corrected orientation during removal of the jig and fitting of the stabilisation plate.

For those tissues which are flexible, the activation of the re-orientation mechanism is typically sufficient to re-orientate the tissue. However, for those tissues that are insufficiently flexible, the tissue may need to be at least partially separated in the region of the tissue about which the rotation is to occur. Accordingly, embodiments may also provide a cutting guide which guides a cutting device when performing such separation. Typically, the cutting device is dimensioned to ensure that the cutting device introduced into the cutting aperture performs the cut at the correct location, in the required orientation, and to the required depth in order to prevent complete severing of the tissue and to avoid any adjacent tissue from being damaged. Given known dimensions of the cutting device, the arrangement of the cutting aperture can also readily be determined using conventional geometric analysis.

Typically, the jig also comprises one or more fixing apertures which are used to drill fixing holes into the tissue. The geometry of these apertures is also such that the location of those holes matches the location of fixing apertures within the stabilisation plate when in the corrected orientation. Furthermore, the orientation of those holes is such that they match the orientation of the apertures in the stabilisation plate so that the fixings enter the tissue at the required angle. Also, the apertures are dimensioned to control the depth of the holes made in the tissue so that these match the length of the fixings used to fix the stabilisation plate in place.

Although it will be appreciated that embodiments may be utilised for a variety of different tissue realignments, such as realigning tendons or other soft tissues, the following embodiments describe an arrangement for correcting the alignment of a bone. Also, although the following embodiment describes a tibia realignment it will be appreciated that other bones can be realigned in a similar way.

High Tibial Osteotomy

High Tibial Osteotomy (HTO) is a realignment procedure for relieving pain and restoring function for early knee osteoarthritis. It can be very effective and is particularly recommended for relatively young patients with early knee osteoarthritis. One of the intentions is to delay the need for joint replacement; young patients have a significantly higher revision rate for joint replacement than older patients. It can also be the definitive treatment for some patients. The current procedure requires inter-operative radiography and there is a risk of not achieving the planned correction. Even for experienced surgeons, the procedure can take a considerable amount of time as care is needed to avoid damaging critical neural and blood vessel structures located at the back of the tibia. Patient dissatisfaction also stems from soft tissue irritation from the implanted stabilisation plate.

Embodiments address these problems by ensuring a precise and reliable correction angle in three dimensions, potentially removing the need for inter-operative radiography and reducing soft tissue irritation risk through anteriorly-located patient-specific stabilisation plates.

Imaging and Modelling

Initially, the tissue to be corrected is imaged. In this example, an X-ray Computed Tomography (CT) scan is taken, with traverse slices at the hip, a detailed scan of the proximal tibia and traverse slices at the ankle.

FIG. 1 shows a representation of such a scan. The image is the anterior view of a patient's left leg, with the medial side to the left and the lateral side to the right. As can be seen from the scan, when extending an axis A between the centre of the femoral head 10 to the centre of the ankle 20 (shown by the vector Vechip-ankle), the centre of the knee joint 30 is misaligned (shown by the vector Vecknee-ankle). Applying a correction angle θ would align the centre of the femoral head 10, the centre of the knee joint 30 and the centre of the ankle 20 along the same axis A. It will be appreciated that a correction angle may also be required in each of the other two planes to provide for a correction in three dimensions.

To provide the correction shown in FIG. 1, an extension to the medial side of the tibia 50 is required. Accordingly, planning software is utilised which holds and displays the tissue image and allows the centre of the femoral head 10, the centre of the ankle 20 and the centre of the knee joint 30 to be designated either automatically or selected. These may then be translated manually in order to determine the correction angles required in each plane, or may be automatically determined by the software.

A region of the proximal tibia 60 to be realigned may be selected either manually or automatically by the software. The geometry of the proximal tibia 60 is segmented from the CT data and a cut 70 to facilitate the realignment is applied. Again, the location and extent of cut 70 may be suggested by the software or determined manually. From this, an osteotomy wedge is then opened virtually at the cut location to the final position in order to generate the required correction. Accordingly, a 3D model is provided of the proximal tibia 60 both in its uncorrected and its corrected forms.

Within the 3D model, the jig is located around the location of the cut 70. Its general size may be selected either manually or automatically by the software. The geometry of the proximal tibia 60 defines the shape of the contacting surface of the jig.

The position, depth and orientation of alignment shafts may then be suggested by the software or manually defined. However, there are restrictions on the alignment of the shafts to ensure that they are compatible with the functioning of the jig. In particular, the alignment shafts must be parallel when the required correction has been applied to the proximal tibia 60. The position, depth and orientation of other fixings may also be suggested by the software or selected manually.

The geometry of the patient-specific operative jig is then generated, which incorporates a patient-specific osteotomy cut guide, together with apertures defining the location, depth and angle of the alignment shafts and other fixings. In particular, as mentioned above, the position and orientation of apertures which receive the alignment shafts are such that those alignment shafts are only parallel once the osteotomy wedge has been opened to provide the required correction. Furthermore, the depth of the holes into the proximal tibia 60 is controlled by varying the length of the apertures. Likewise, the depth, extent and orientation of the cut 70 is controlled by the orientation, length and depth profile of the cut guide. In particular, the jig is designed assuming a particular length of drill bit and cutting blade. The depth of the apertures can then be varied to vary the depth of the hole made by the drill bit. This helps to ensure that the correct depth holes are made, in order to prevent damage to any adjacent tissue and avoid the need for any operative measurement or imaging. A reorientation mechanism is designed which displaces the two parts of the jig with respect to each other to open the osteotomy wedge to provide the required correction. Wedges are designed which engage with apertures in the jig and which extend into the cut 70 to maintain the opened osteotomy wedge to maintain the required correction.

Although embodiments may provide a generically-shaped surface to be received on the medial side of the femur 50, in this embodiment the femur-engaging surface of the jig is precisely contoured to the patient's bone and will only fit at the correct location on the proximal tibia 60 initially in its uncorrected configuration. This helps to further improve the precision of the correction.

The jig is then typically 3D printed from this model.

The stabilisation plate is designed with alignment apertures which will align with shafts located in the proximal tibia 60 by the jig only when the required correction has been maintained. Also, the location and orientation of the other fixing holes in the tibia only align with the fixing apertures in the stabilisation plate when the required correction is achieved. Typically, the stabilisation plate is designed with annular abutments upstanding from the surface facing the proximal tibia in order to cause the main surface of the stabilisation plate to stand off the proximal tibia 60.

In this embodiment the stabilisation plate is precisely contoured to the patient's bone and will only fit at the correct location on the proximal tibia 60 in its corrected configuration. This helps to further improve the precision of the correction.

The stabilisation plate is then typically 3D printed from this model.

Embodiments also provide an elongate stirrup arrangement (not shown) which may be used to facilitate the correct location of the jig on the tibia. The stirrup arrangement extends from a coupling which is received by the patient's ankle to a coupling which engages with the jig. The length of the elongate stirrup is such that it positions the jig at the correct location, with the final positioning being achieved by the tissue-engaging surface.

The elongate stirrup arrangement is then typically 3D printed from this model.

Correction Procedure

Jig Fixing

The surgeon makes a skin incision, the soft tissue is retracted and the jig, generally 100, is located either directly or with the assistance of the elongate stirrup arrangement. The contoured surface causes the jig to be precisely located. This enables the jig to be located without needing any further measurement or imaging.

Referring to FIG. 1 (which shows the jig 100 located on the medial side of the proximal tibia 60, with and opened osteotomy wedge following the cut 70), using a defined length drill bit, the drill bit is introduced into the fixing apertures B and holes drilled. The upper portion 100A of the jig 100 is then secured in place using K-wires or other similar temporary fixings (not shown).

Again, using a selected length drill bit, the drill bit (not shown) is placed in to the alignment apertures A and the bone is then drilled. In this example, the drill bits are then left in the drill holes to secure the bottom portion 100B of the jig 100 to the proximal tibia 60.

Figure 2:
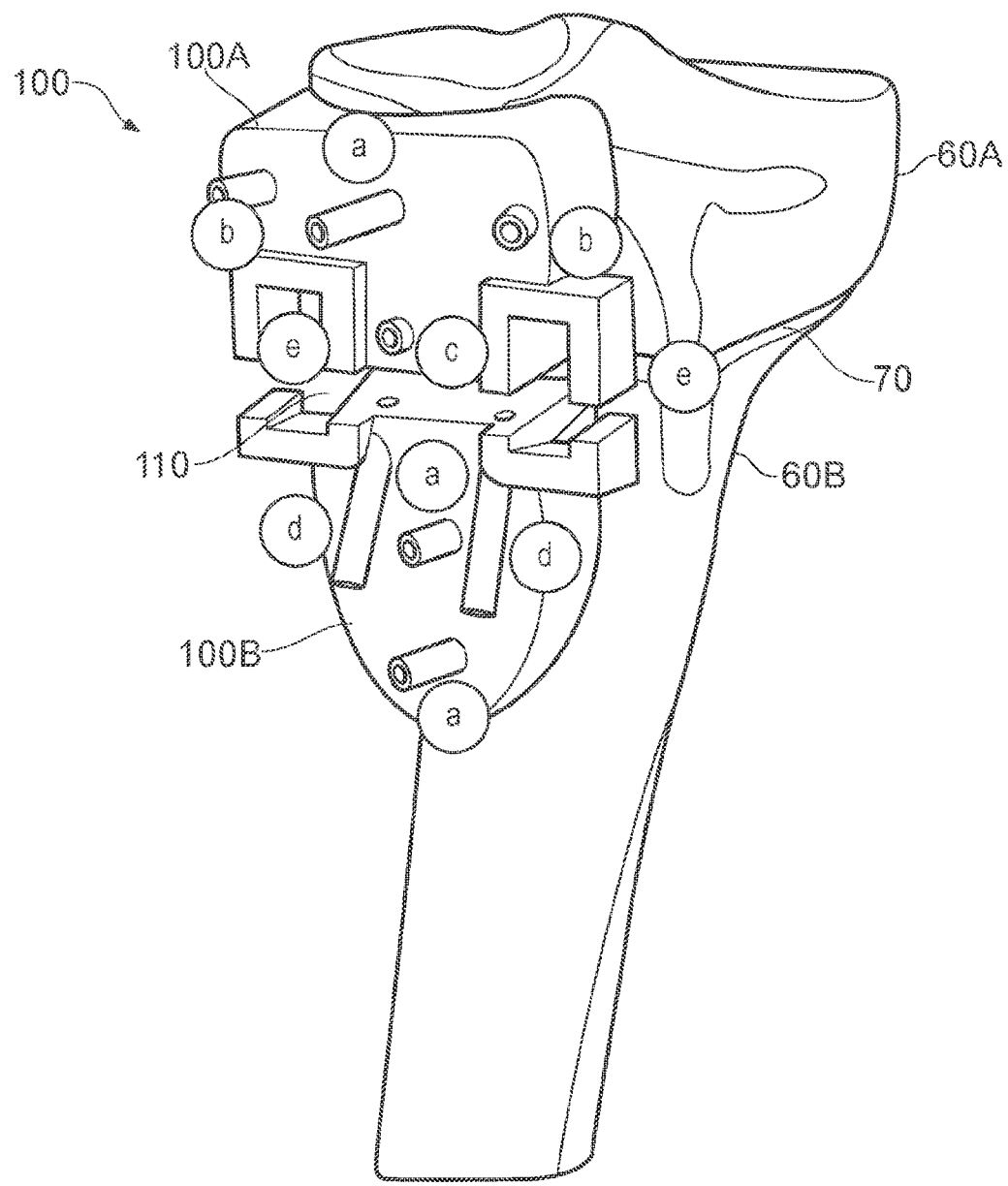
FIG. 2 show a jig according to one embodiment located on the tissue with the tissue correction applied.

As shown in FIG. 2, all the retained drill bits in the alignment apertures A will be parallel to each other when the jig is in the fully open position. However, it will be appreciated that these drill bits will be non-parallel prior to the osteotomy wedge being opened, and this also helps to retain the jig in position.

The fixing aperture C also receives a selected length drill bit and a hole is drilled, but left empty.

Osteotomy Cut

The secured jig 100 (which is still a single unit) then provides maximum stability to guide a saw during the cut 70 on the proximal tibia 60. In this embodiment, the cutting aperture 110 is dimensioned to receive a conventional plunge-cut reciprocating orthopaedic saw. The location and orientation of the cutting aperture 110 is selected to ensure that the cut occurs at the correct location on the proximal tibia 60. Furthermore, the depth of the cutting aperture 110 is selected based on a selected depth of cutting blade. The depth profile of the cutting aperture 110 is typically varied to vary the depth of the cut in to the proximal tibia 60 in order, typically, to retain a connecting hinge portion of the tibia, joining the upper proximal tibia portion 60A to the lower proximal tibia portion 60B. Controlling the depth of the cut by varying the depth of the cutting aperture also helps to ensure that possible damage to adjacent tissue is avoided. Accordingly, the cutting aperture or cut guide has walls that prevent the saw blade from breaching the posterior region containing the critical neural and blood vessel structures. Again, this enables the required cut to be made without needing any further measurement or imaging.

Applying Correction

Once the cut has been made, two fixed length, flat ended screws (not shown) are then actuated in the jig-opening screw guides D, which open the osteotomy wedge to the required correction when the screws are fully tightened. The upper portion 100A is provided with reinforced recesses (not shown) with tapered edges that guide the jig-opening screws. A connection (not shown) between the top portion 100A and the bottom portion 100B of the jig 100 is broken to allow the two portions to separate. The position and orientation of the jig-opening screw guides D and the length of the inserted screws is selected to re-orientate the upper proximal tibia 50A with respect to the lower proximal tibia 50B by the required correction. The re-orientation typically increases the distance between the upper proximal tibia 50A and the lower proximal tibia 50B, in this example extending the medial length of the tibia 50, together with the appropriate change to the posterior and/or anterior lengths of the tibia 50 in order to perform the required correction. Again, this enables the required correction to be made without needing any further measurement or imaging.

Supporting Correction

Figure 3:
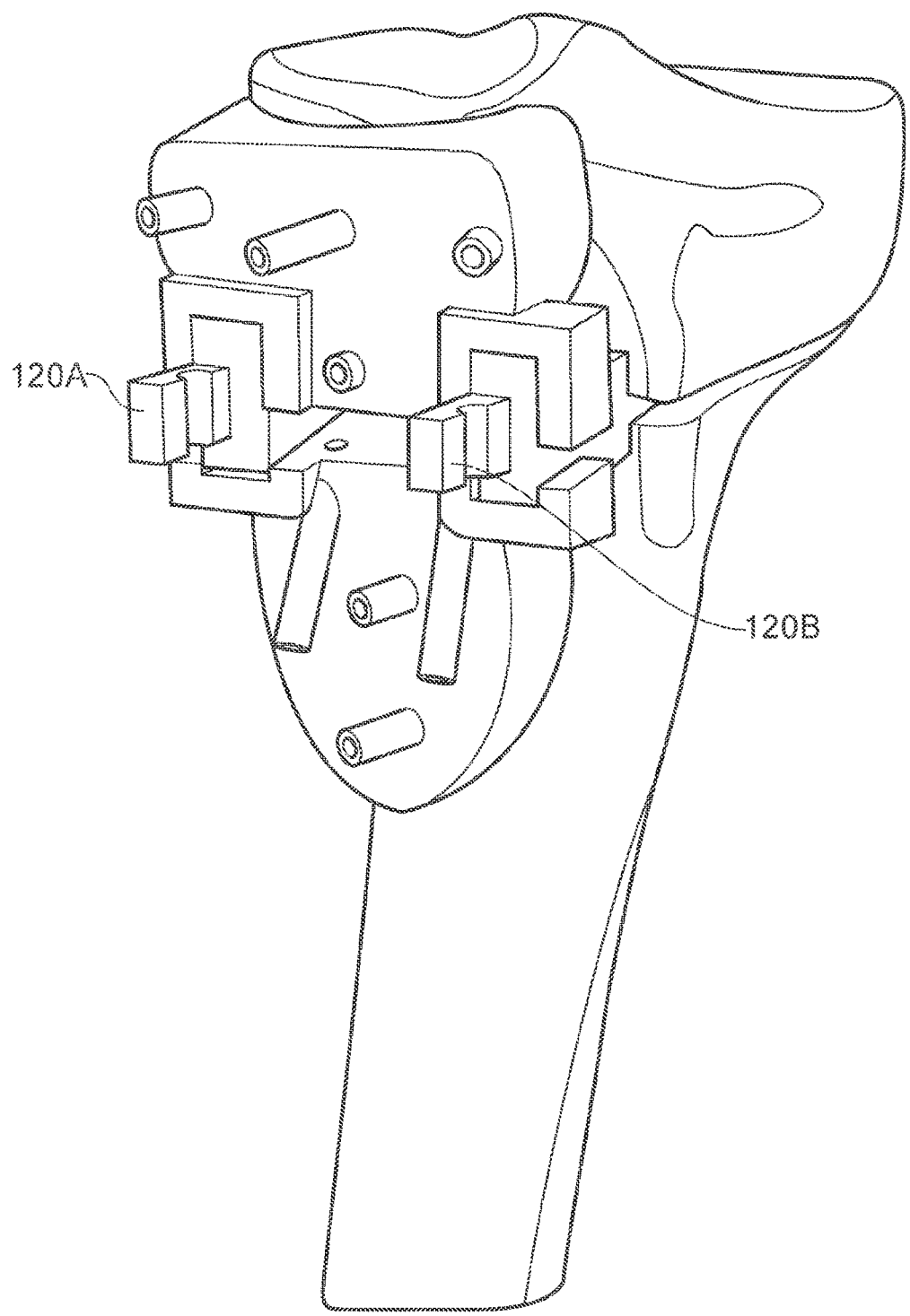
FIG. 3 shows the jig with wedges inserted.

As shown in FIG. 3, in this example, two retaining wedges 120A, 120B are then received within matching apertures E in the jig 100. The wedges 120 can only be inserted into the apertures E when the required correction has been made. The wedges have a portion which is received within the apertures and which then abuts the proximal tibia 60. The wedges 120A, 120B also have a wedge portion which extends into the opened tibia cut. The wedges 120A, 120B are dimensioned to only fit in one of the apertures E to prevent incorrect placement. Once located in the wedge apertures E, the wedges 120A, 120B hold the tibia cut open. The wedges 120A, 120B are also keyed to ensure the correct vertical orientation. The geometry of the jig 100 is designed such that the direction of the wedge insertion slots E are also parallel to the axis of the alignment apertures A when the required correction to the proximal tibia 60 has been made.

Jig Removal

Figure 4:
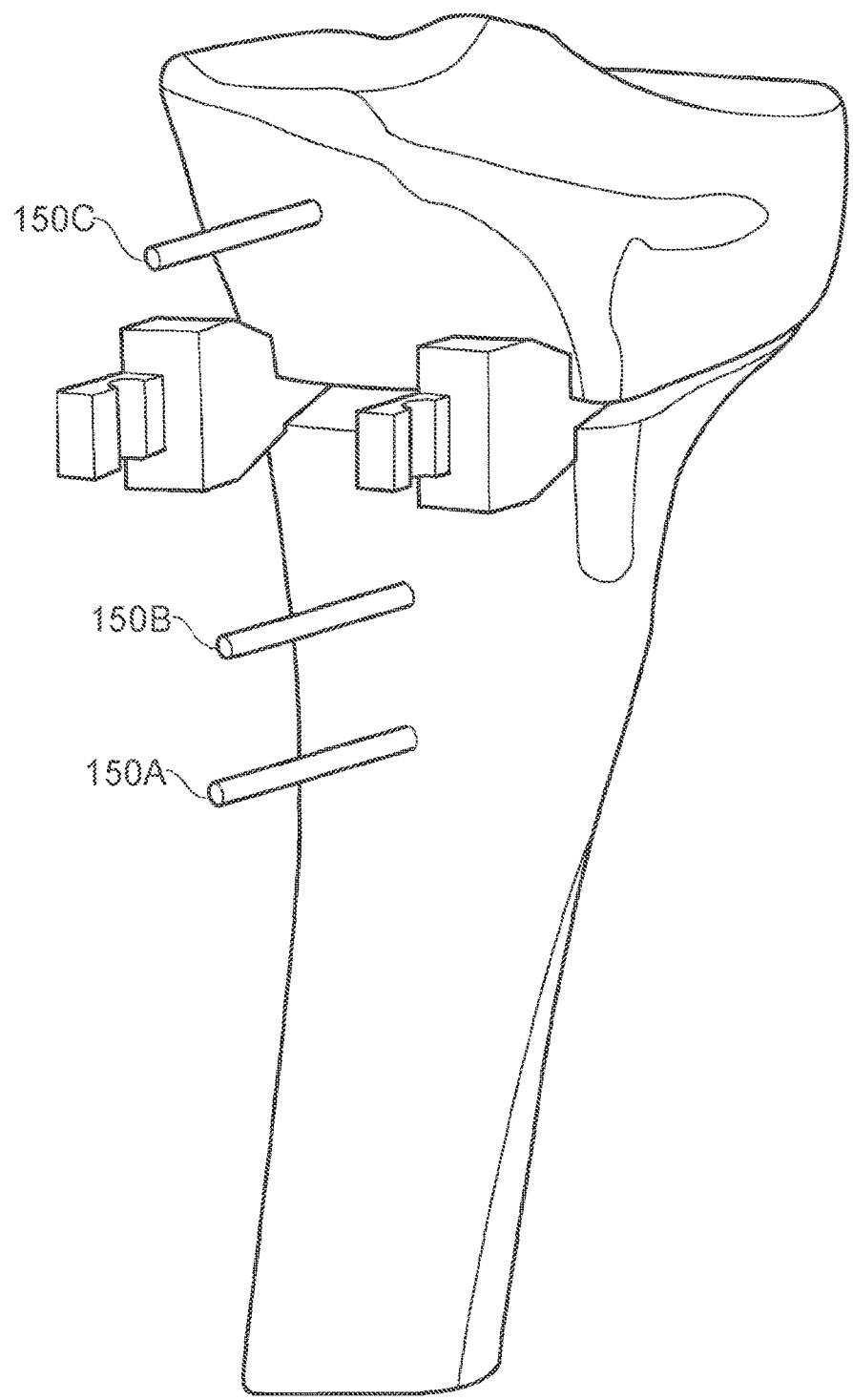
FIG. 4 shows the jig removed with the wedges and alignment shafts retained.

With the wedges 120A, 120B in position, the jig-opening screws can now be untightened and the K-wires removed. Only the drill bits 150A-C in the alignment apertures A now remain. This allows the removal of the jig in two sections, leaving the wedges 120A, 120B holding open the cut, as shown in FIG. 4.

Stabilisation Plate Fitting

Figure 5:
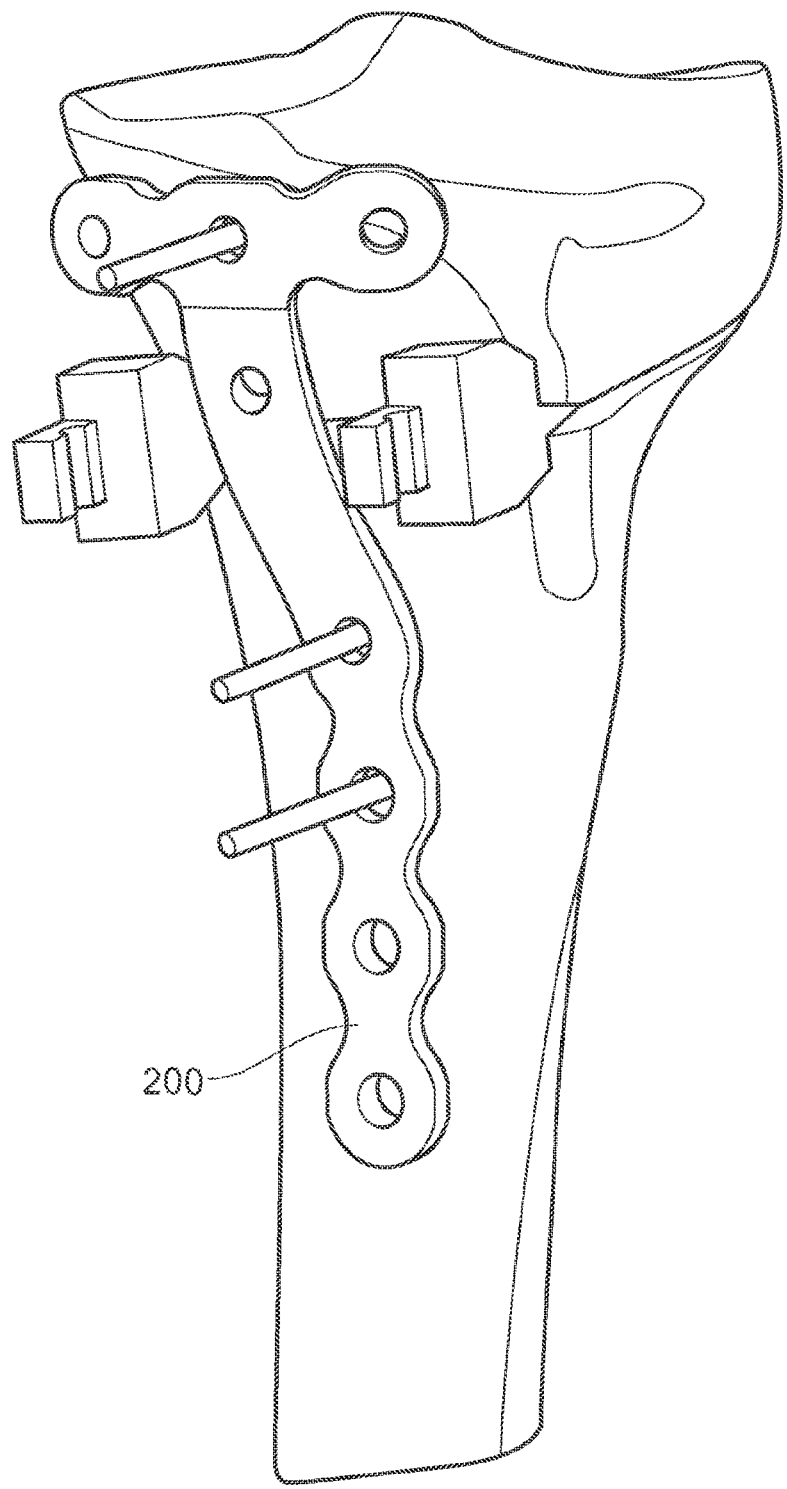
FIG. 5 shows fitting of a stabilisation plate according to one embodiment.

As shown in FIG. 5, the stabilisation plate 200 can now be positioned with the alignment apertures in the plate fitting the three drill bits 150A-C. The plate 200 will only fit on the drill bits 150A-C should the correction factor continue to be correctly applied. Again, this ensures that the required correction continues to be made without needing any further measurement or imaging.

Figure 6:
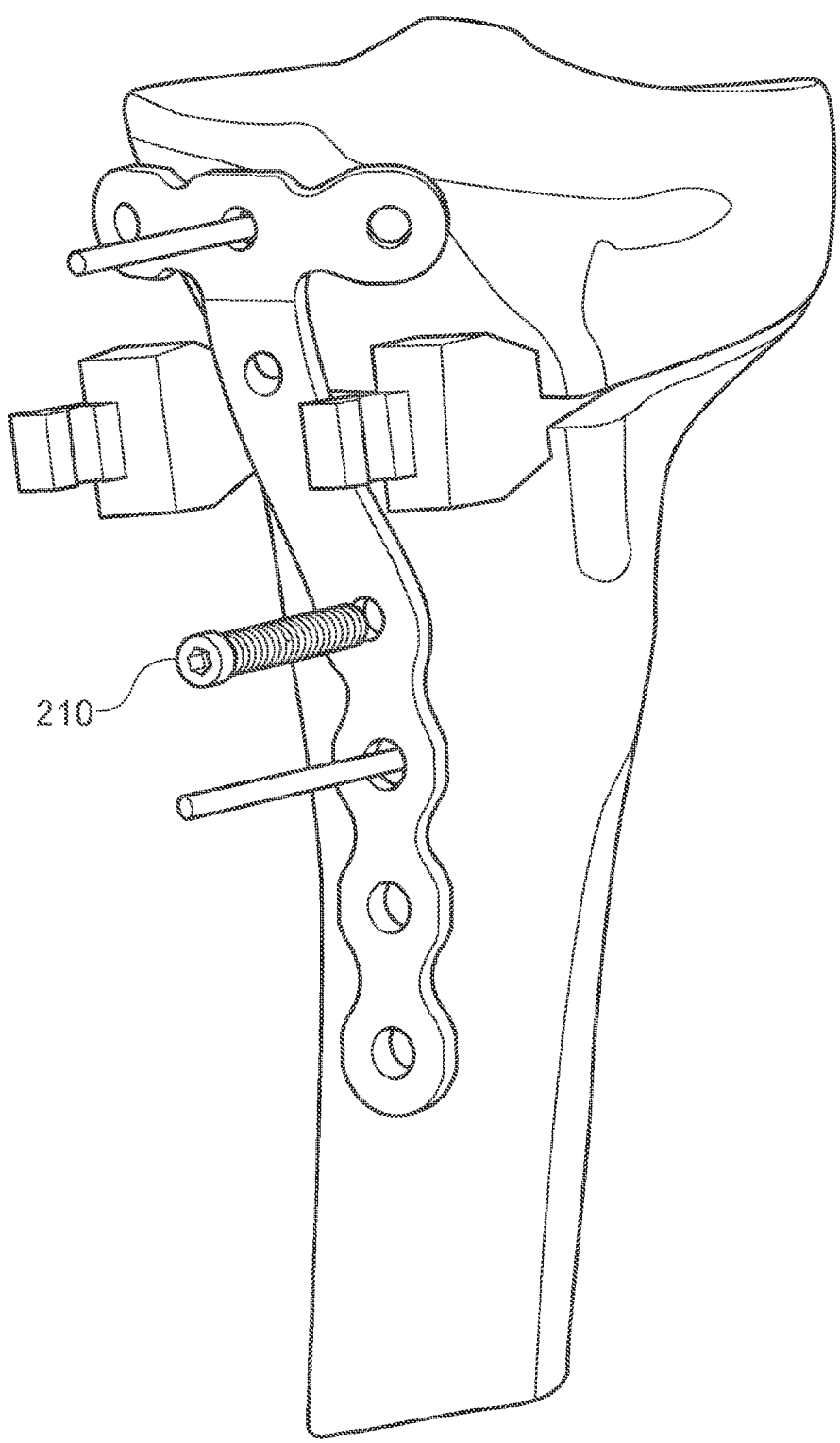
FIG. 6 shows fitting of fixings to the stabilisation plate.

As shown in FIG. 6, locking screws 210 can now be inserted to secure the plate 200 to the bone. Typically, the central drill bit 150B is first removed and a suitably dimensioned locking screw is inserted.

Next, the proximal drill bit 150C and then the distal drill bit 150A are replaced with locking screws. The remaining locking screws are inserted into the pre-drilled holes. The two most distal screws are inserted last; this can be done using small incisions above the respective plate apertures. Typically, each locking screw will be dimensioned to fit the hole provided and they may be uniquely identified to be associated with a corresponding uniquely identified aperture in the stabilising plate 200.

Figure 7:
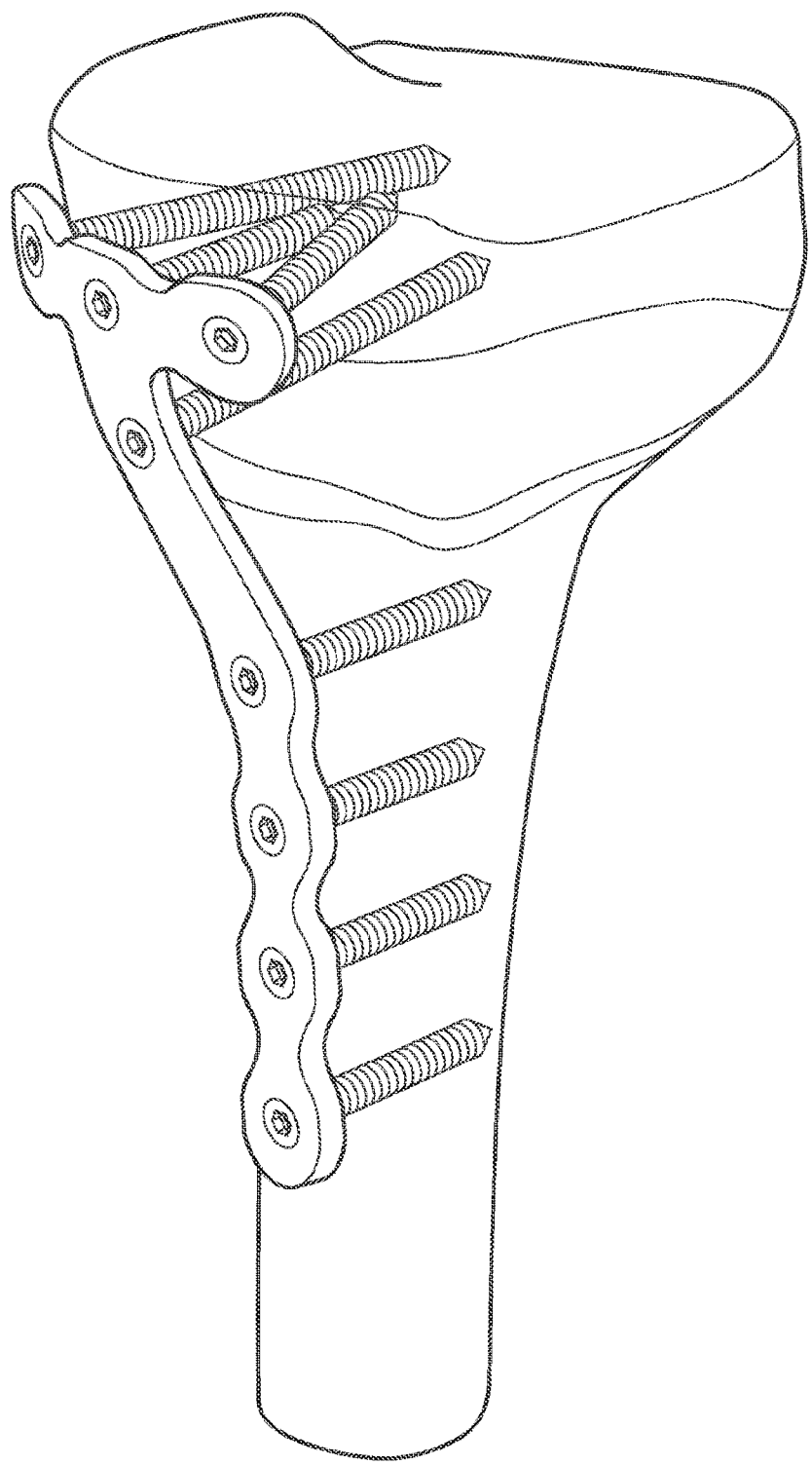
FIG. 7 shows the stabilisation plate fitted.

Finally, the wedges can be removed and the operation can then be completed by skin closure as shown in FIG. 7.

It will be appreciated that although, in the embodiments described above, drill bits are used as alignment shafts and are removed, other fixings may be used as the alignment shafts and these may remain in place and be cut to length with an appropriate fixing on their upstanding surface. Also, it will be appreciated that none of the apertures necessarily need to be axially aligned and may well be displaced in order to improve fixing in to the tibia.

Accordingly, embodiments provide a structurally optimised patient-specific High Tibial Osteotomy locking plate that has several aspects that make it unique:

1. The profile of the plate is precisely matched to the patient using a CT-scan of the affected limb and the creation of a virtual model. The plate is additively manufactured from titanium allowing a unique plate geometry to be produced for every patient.

2. The virtual model allows the position of the screws to be customised. The angles of the threaded holes within the plate are then precisely matched to the customised screw positions. The plate will be manufactured so that the screws are inserted at the pre-defined angle and the head of the screws is flush against the plate so as to not protrude.

3. The profile of the plate is structurally optimised using patient-specific information such as weight, activity level and bone quality. The algorithm will ensure that the plate has appropriate stiffness and strength characteristics while minimising the distance the plate will protrude from the surface of the bone.

Customised software helps the surgeon plan the procedure. Precise angular correction (in three dimensions) can then be specified and visualised. Custom guides that match the patient's anatomy (manufactured using rapid-prototyping technology) will be used to make the osteotomy cuts and position the tailored plate. Reproducibility of the alignment is, therefore, improved while removing the reliance on intraoperative radiology to achieve the alignment.

The software allows the length of each of the required screws will be obtained pre-operatively. The angle of the screws with respect to the plate is also modifiable. By providing the specifics of all implants involved, this removes the need for intraoperative measurements. The tailored implants (plate and screws) will be sterilised and shipped to the health provider 'just-in-time' for the procedure. As the implants will fit precisely to the patient's profile, intraoperative radiology will no longer be required. Benefits include: reduced surgical time and a reduced the risk of soft tissue irritation. Additionally, health providers will not need to stock large numbers of HTO implants.

Figure 8:
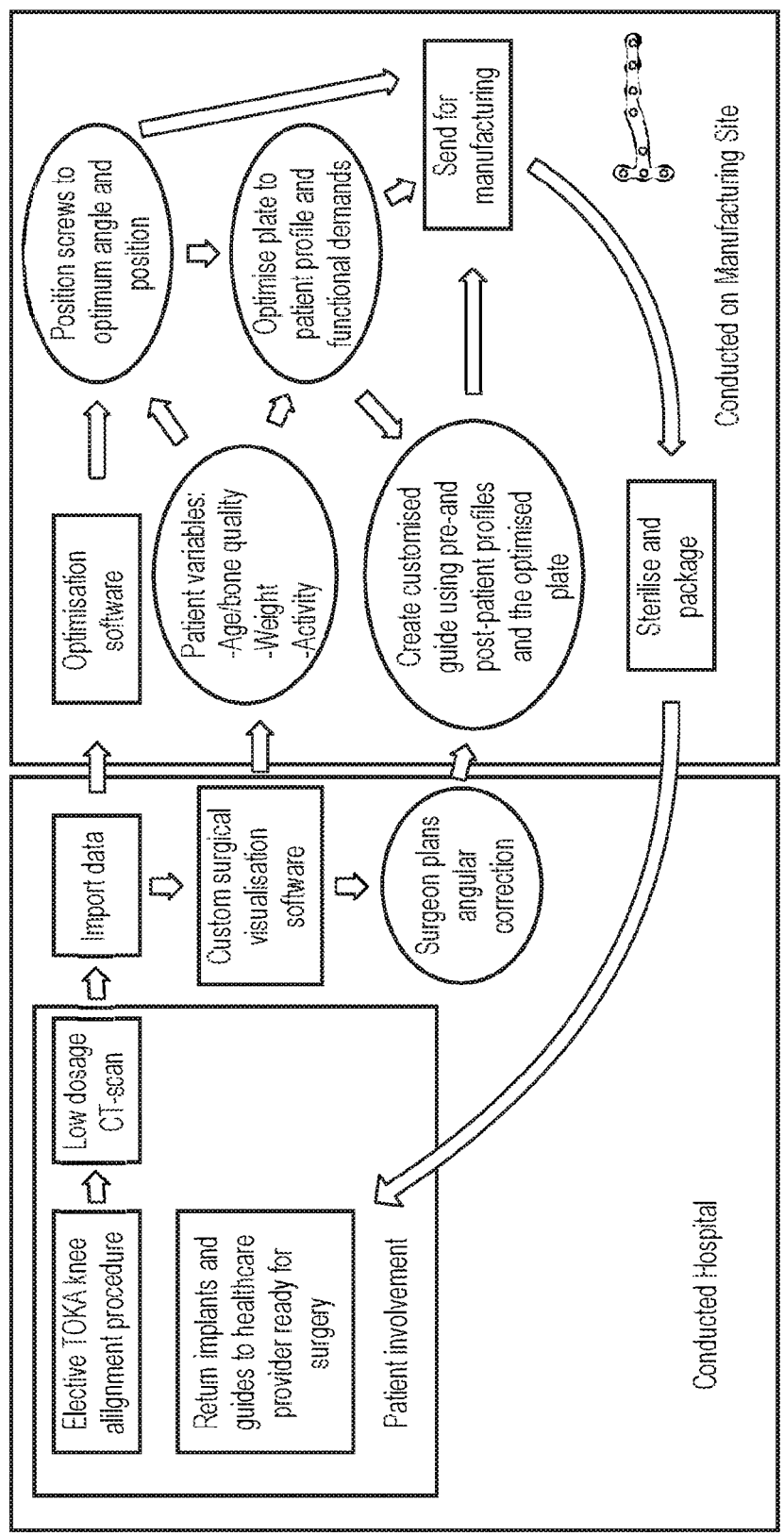

The order of the workflow is shown in FIG. 8.

In will be appreciated that all the procedure will generally be used for tibial osteotomies, however, the methodology could easily be applied to femoral and other osteotomies.

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc.

Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Further, it should be noted that terms of approximation (e.g., "about", "substantially", "approximately", etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

Thus, the present invention is well adapted to carry out the objects and attain the ends and advantages mentioned above as well as those inherent therein. While the inventive device has been described and illustrated herein by reference to certain preferred embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

What is claimed is:

1. A surgical assembly, comprising:
    a jig comprising:
    a body having a tissue-engaging surface shaped to be received by tissue to be re-orientated by a correction factor comprising two or more correction angles, wherein said body comprises:
    a first body portion shaped to be received by a first tissue portion of said tissue; and
    a second body portion shaped to be received by a second tissue portion of said tissue, said first body portion being re-orientatable with respect to said second body portion to re-orientate said first tissue portion with respect to said second tissue portion by said correction factor;
    wherein said body defines a plurality of alignment apertures, said first body portion defining at least one of said plurality of alignment apertures and said second body portion defining at least one of said plurality of alignment apertures; and
    wherein said plurality of alignment apertures are orientated to be divergent in an uncorrected position prior to application of said correction factor and to be parallel in a corrected position on application of said correction factor.

2. The assembly of claim 1, wherein each alignment aperture has a length selected to control a depth of an associated alignment shaft into said tissue.

3. The assembly of claim 1, wherein said jig defines a cutting aperture shaped to receive a cutting device operable to at least partially divide said tissue into said first tissue portion and said second tissue portion.

4. The assembly of claim 3, wherein said cutting aperture is positioned between said first body portion and said second body portion.

5. The assembly of claim 4, wherein a depth of said cutting aperture is dimensioned to retain a hinge portion joining said first tissue portion with said second tissue portion.

6. The assembly of claim 4, wherein said depth of said cutting aperture is varied to retain said hinge portion joining said first tissue portion with said second tissue portion.

7. The assembly of claim 3, wherein said cutting aperture is orientated to orientate said cutting device with respect to said tissue.

8. The assembly of claim 3, wherein said cutting aperture extends between said tissue-engaging surface and an interaction surface opposing said tissue-engaging surface.

9. The assembly of claim 1, wherein said body comprises at least one wedge aperture dimensioned to receive a wedge.

10. The assembly of claim 9, wherein said wedge aperture is positioned between said first body portion and said second body portion.

11. The assembly of claim 9, comprising at least one wedge dimensioned to be received by a corresponding wedge aperture.

12. The assembly of claim 11, wherein said wedge comprises a receiving portion dimensioned to be received by said corresponding wedge aperture and a protruding portion dimensioned to extend into said tissue to retain said correction factor.

13. The assembly of claim 12, wherein said wedge comprises an abutment portion coupling said receiving portion and said protruding portion and operable to engage with a facing surface of said tissue.

14. The assembly of claim 1, wherein said body comprises a retention portion operable to retain said first body portion with said second body portion until separated.

15. The assembly of claim 1, wherein said body comprises at least one fixing aperture arranged to receive a shaft to engage with said tissue and wherein the fixing aperture has a length selected to control a depth of said shaft into said tissue.

16. The assembly of claim 15, comprising: a stabilisation plate having plate alignment apertures positioned to receive said shaft on application of said correction factor to said tissue.

17. The assembly of claim 16, wherein said stabilisation plate comprises plate fixing apertures positioned to align with voids created by said shafts on application of said correction factor to said tissue.

18. The assembly of claim 1, wherein each alignment aperture is arranged to receive an alignment shaft to engage with said tissue.

19. The assembly of claim 1, wherein said plurality of alignment apertures are each orientated to orientate with an associated alignment shaft to be divergent in said uncorrected position prior to application of said correction factor and to be parallel in a corrected position on application of said correction factor.

* * * * *